United States Patent [19]

Kleiner et al.

[11] Patent Number: 6,087,423
[45] Date of Patent: *Jul. 11, 2000

[54] 1-HYDROXYDIHYDROPHOSPHOLE OXIDES AND 1-HYDROXY-PHOSPHOLANE OXIDES, PREPARATION THEREOF AND USE THEREOF AS FLAME RETARDANTS

[75] Inventors: Hans-Jerg Kleiner, Kronberg; Winfried Budzinsky; Günther Kirsch, both of Bad Soden, all of Germany

[73] Assignee: Ticona GmbH, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/810,656

[22] Filed: Mar. 3, 1997

[30] Foreign Application Priority Data

Mar. 4, 1996 [DE] Germany .............. 196 08 011

[51] Int. Cl.$^7$ ..................... C08K 5/49
[52] U.S. Cl. ........................... 524/116; 523/351
[58] Field of Search ............... 524/116; 523/351

[56] References Cited

U.S. PATENT DOCUMENTS

| | | |
|---|---|---|
| 3,900,444 | 8/1975 | Racky et al. . |
| 4,036,811 | 7/1977 | Noetzel et al. . |
| 4,208,322 | 6/1980 | Sandler . |
| 4,221,874 | 9/1980 | Moedritzer .............. 524/116 |
| 4,268,432 | 5/1981 | Maslen et al. .......... 523/351 |
| 4,471,080 | 9/1984 | Rinaldi et al. .......... 523/351 |

FOREIGN PATENT DOCUMENTS

| | | |
|---|---|---|
| 700042 | 12/1967 | Belgium . |
| 0699708 | 3/1996 | European Pat. Off. . |
| 2252258 | 5/1974 | Germany . |
| 2447727 | 4/1976 | Germany . |
| 2915116 | 10/1979 | Germany . |

OTHER PUBLICATIONS

Journal of Polymer Science: Part A–1, vol. 6, 1975–1990 (1968); Metal Coordination Polymers. I. Synthesis and Thermogravimetric Analysis of Beryllium Phosphinate Polymers; P.J. Slota, Jr., L.P. Freeman, and N.R. Fetter.

*Primary Examiner*—Veronica P. Hoke
*Attorney, Agent, or Firm*—Connolly Bove Lodge & Hutz LLP

[57] ABSTRACT

Salts of 1-hydroxydihydrophosphole oxides and 1-hydroxyphospholane oxides and use thereof as flame retardants. The salts of 1-hydroxydihydrophosphole oxides and 1-hydroxyphospholane oxides are useful as flame retardants, especially for plastics such as polyester or polyamide. The aluminum salts are preferred.

17 Claims, No Drawings

1-HYDROXYDIHYDROPHOSPHOLE OXIDES AND 1-HYDROXY-PHOSPHOLANE OXIDES, PREPARATION THEREOF AND USE THEREOF AS FLAME RETARDANTS

Salts of 1-hydroxydihydrophosphole oxides and 1-hydroxy-phospholane oxides, preparation thereof and use thereof as flame retardants This invention relates to salts of 1-hydroxydihydrophosphole oxides and 1-hydroxyphospholane oxides. An aspect of this invention relates to moldable flame-retardant polymer or plastic materials and shaped articles made from these materials, including specific components such as electrical, electronic, or mechanical components. Another aspect of this invention relates to fire-protective coatings useful for application to various objects or substates.

BACKGROUND OF THE INVENTION

Polymers are frequently rendered flame-resistive by adding phosphorus and halogen compounds or mixtures thereof to them. Some polymers are processed at high temperatures, for example at 250° C. or higher. For this reason, many known flame retardants are unsuitable for such applications, since they are too volatile or are not sufficiently heat-resistant.

Alkali metal salts of phosphinic acids are known as flame-retardant additives for polyamide molding materials (DE-A1-2 447 727). However, they tend to exhibit corrosion effects.

It is an object of the present invention to provide flame retardants which do not have the disadvantages of existing flame retardants. For example, the flame retardants shall be simple and inexpensive to prepare and possess good flame retardancy and also high temperature resistance (e.g. resistance to temperatures of at least 250° C.).

SUMMARY OF THE INVENTION

It has now been found that, surprisingly, salts of 1-hydroxydihydrophosphole oxides and/or 1-hydroxyphospholane oxides possess excellent flame retardancy in thermoplastic polymers such as polyamides or polyesters.

The present invention accordingly provides salts of 1-hydroxydihydrophosphole oxides and/or 1-hydroxyphospholane oxides, processes for preparing them and their use as flame retardants.

The present invention further provides molding materials comprising a plastic (preferably a thermoplastic) and at least one salt of a 1-hydroxydihydrophosphole oxide and/or 1-hydroxyphospholane oxide.

The preferred salts are the salts of 1-hydroxydihydrophosphole oxides of the formula (Ia) or formula (Ib) and salts of 1-hydroxyphospholane oxides of the formula (II)

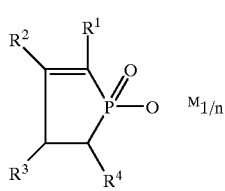
(Ia)

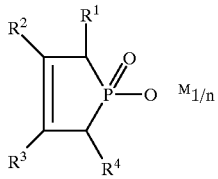
(Ib)

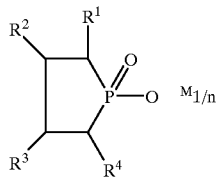
(II)

where

| | |
|---|---|
| $R^1$, $R^2$, $R^3$ and $R^4$ | are each hydrogen or a straight-chain or branched alkyl radical, preferably a straight-chain or branched $C_1$–$C_{12}$-alkyl radical, particularly preferably $C_1$–$C_4$-alkyl radical, especially methyl or ethyl; and |
| M | is a metal of the second or third main or sub group of the Periodic Table, especially magnesium, calcium, zinc or aluminum; and |
| n | is the valence of M, preferably 1, 2 or 3. |

The above-described salts of 1-hydroxydihydrophosphole oxides and 1-hydroxyphospholane oxides have flame retardant properties and will hereinafter be referred to collectively as the salts or as the flame-retardant salts.

Examples of flame-retardant salts which are particularly suitable for the purposes of the invention are the metal salts of 1-hydroxy-3-alkyl-2,3-dihydro-1H-phosphole 1-oxide, 1-hydroxy-3-methyl-2,5-dihydro-1H-phosphole 1-oxide, 1-hydroxy-2,3-dihydro-1H-phosphole 1-oxide, 1-hydroxy-2,5-dihydro-1H-phosphole 1-oxide, 1-hydroxy-1H-phospholane 1-oxide and 1-hydroxy-3-methyl-1H-phospholane 1-oxide and also mixtures of these salts. The metal which provides the cations of these salts is preferably a metal of the second and third main or sub groups of the Periodic Table of the Elements, particularly Group IIA, Group IIB, and/or Group IIIA, e.g. the alkaline earth metal salts (Group IIA), especially magnesium. Zinc is the preferred metal of Group IIB, and aluminum is the preferred metal of Group IIIA. Particularly good results have been obtained with the aluminum salts.

The salts can be prepared from 1-hydroxydihydrophosphole oxides and 1-hydroxyphospholane oxides in aqueous solution by reaction with the corresponding metal carbonates, metal hydroxides or metal oxides. For this purpose, 1-hydroxydihydrophosphole oxides and/or 1-hydroxyphospholane oxides are generally dissolved in water and advantageously admixed with stoichiometric amounts of the corresponding metal hydroxide, metal carbonate or metal oxide by stirring. The reaction mixture is then generally heated, preferably to a temperature from 30 to 150° C., in particular 70 to 110° C., and stirred for several hours. The reaction times range from a few hours (at least 10 hours) to several days (1 to 7 days). After the reaction has ended, the reaction mixture is worked up by conventional methods (cooling, filtration with suction, washing, drying, etc.).

The starting compounds are known in the art (e.g. 1-hydroxydihydrophosphole oxides) and are obtainable by known methods (e.g. from the 1-chlorodihydrophosphole oxides), which can be prepared for example as described in EP-A1-0452755. The 1-chlorodihydrophosphole oxides can be hydrogenated to prepare the 1-hydroxyphospholane oxides.

The salts of this invention are generally thermally stable. They do not decompose the polymers on incorporation into them and do not adversely affect the processing to make the molding material, notwithstanding the use of elevated temperature processing conditions such as temperatures of at least 250° C. The salts are essentially non-volatile under the customary manufacturing and processing conditions for thermoplastics (including elevated temperature conditions such as those mentioned above). They exhibit excellent flame retardancy.

The preferred plastic (herein also referred to as the polymer) is moldable and hence is essentially thermoplastic or of such low crosslink density that it can be melted and, if necessary, remelted without substantial change in the polymer structure. Preferred plastics are condensation polymers such as polyesters and/or polyamides, for example nylon 46 or nylon 66 in the case of polyesters, and polyethylene terephthalate (PET) or polybutylene terephthalate (PBT) in the case of preferred polyesters.

Polyamides and polyesters which can be used for the purposes of this invention are described for example in "Ullmann's" encyclopedia of industrial Chemistry, ed. Barbara Elvers, Vol. A21, chapter Polyamide (p. 179–205) and chapter "Polyesters (p. 227–251), VCH, Weinheim-Basel-Cambridge-New York 1992", incorporated herein by reference.

The amount of salt to be added to the polymer can vary within wide limits. In general, 5 to 30% by weight, preferably 10 to 20% by weight, are used, based on the polymer. The most suitable amount depends on the nature of the polymer and the nature of the salt used and can be readily ascertained by experimentation.

The flame-retardant salts can be used in various physical forms, depending on the nature of the polymer used and the desired properties. For instance, they can be ground to a finely divided form, for example for achieving a better dispersion in the polymer. If desired, it is also possible to use mixtures of various salts.

A flame-retardant salt can be incorporated into the polymer by a variety of known techniques. In the context of this invention, "incorporating" the flame-retardant salt is thus not limited to any specific physical combination procedure or any particular phase of the polymer (molten, solid, pre-polymeric, etc.), but chemical incorporation (where, for example, a salt is linked into the polymer molecule) is not required; physical combinations of the salt and the polymer provide the desired benefits of this invention.

In one preferred physical combining procedure, the polymer and the salt are mixed together; the polymer portion of the resulting mixture is melted in a compounder (a twin-screw extruder, for example); and the flame-retardant salt is homogenized in the polymer melt. The melt can be extruded, cooled and granulated. The salt can also be metered directly into the compounder.

It is ordinarily especially convenient to incorporate the salt in a form which is as compatible as possible with the polymer or plastic to be rendered flame retardant. Such especially convenient forms include particulate plastic masses (particularly plastic granules) containing a minor amount of the salt or particulate (e.g. granular) masterbatches containing much higher percentages of salt (e.g. 30 to 80 or 90% by weight, based on the weight of the masterbatch). In these forms, the flame-retardant salt can be mixed into a polymer which lacks flame-retardant properties. Moreover, finished granular polymer containing the desired amount of flame-retardant salt (e.g. 5 to 30% by weight of the polymer) can serve as a suitable molding material without further modification. For example, a mass of such granular polymer can be processed directly on an injection molding machine.

Alternatively, a mixture can first be melted in an extruder, granulated, and processed after drying.

Incorporation of the flame-retardant salts can also be accomplished in condensation-polymerized plastics, e.g. in polyesters, during an early stage in the manufacture of the product, e.g. during the polycondensation. In this or any of the other incorporation procedures, the product which results is a flame-retardant plastic or polymer, typically in the form of a moldable material or in the form of a material which has already been shaped.

The flame-retardant plastic or polymer can contain, in addition to a flame-retardant salt or mixture of salts, a variety of conventional components which provide or alter the color, the stability, the physical properties of the plastic, and the like.

The use of these known ingredients is well known and need not be described in detail. Thus, the polymers can also have added to them fillers and reinforcing materials such as glass fibers, glass balls or minerals such as chalk, UV stabilizers, lubricants, colorants, pigments, nucleating agents, antistatic agents, or various combinations of these components.

The plastics, such as polyamides and polyesters, rendered flame-retardant using one of the aforementioned flame-retardant salts are typically in the form of a molding material and thus are useful for manufacturing shaped articles, which broadly includes films, coatings on substrates, filaments and fibers as well as more massive three-dimensional objects. Typical molding procedures useful in this invention include injection, extrusion or press molding.

Flame retardant salt-containing plastics, especially polyesters and polyamides, are notable for a high tracking current resistance (high CTI). Accordingly, shaped objects made in accordance with this invention can include a wide variety of electrical, electronic, and mechanical (including electro-mechanical) components. Examples of such components include:

Coil formers, transformers, relays, switches, plug connectors, motors and motor parts (rotors, bearing plates, etc.), molded interconnection devices (MIDs), bases (e.g. SIMM bases), mechanical components in electrical and household appliances, for example gearwheels, levers, camshafts, spacers, hinges, sliding bearings, housings, coverings, sheathings and coatings of electrical devices and appliances, for example capacitor housings, relay housings, capacitor covers, cable sheathings.

Further examples of shaped articles include plugs, mounts, housings, coverings, sheathings, overcoatings. Coatings can be applied to a variety of known substrates.

Thus, flame-retardant salts can also be included in coatings such as fire protection coatings, especially fire protection coatings for plastics such as polyoxymethylene, polyester or polyamide.

The invention accordingly also provides for the use of the flame-retardant salts as a constituent of coatings, especially of fire protection coatings.

The present invention accordingly also provides for the use of salts of 1-hydroxydihydrophosphole oxides and/or 1-hydroxyphospholane oxides in coatings, especially fire protection coatings.

EXAMPLES

1. Preparation of the Salts 1.1. Preparation of the aluminum salt of 1-hydroxy-2,5-dihydro-1H-phosphole 1-oxide 105 g (0.89 mol) of 1-hydroxy-2,5-dihydro-1H-phosphole 1-oxide are dissolved in 250 g of water and mixed with 23.1

(0.297 mol) of aluminum hydroxide by stirring. The mixture is then heated to 90° C. and stirred at 90° C. for 24 hours. It is then cooled down and filtered with suction, and the filter residue is washed with water. Drying in a vacuum drying cabinet to 150° C. leaves 111.5 g of a white powder which has no melting point below 360° C. The yield is about 100% of theory.

1.2. Preparation of the aluminum salts of a mixture of 1-hydroxy-2,5-dihydro-1H-phosphole 1-oxide and of 1-hydroxy-2,3-dihydro-1H-phoophole oxide 901 g (7.63 mol) of a mixture of 1-hydroxy-2,5-dihydro-1H-phosphole 1-oxide and 1-hydroxy-2,3-dihydro-1H-phosphole oxide in a molar ratio of about 1:1 are dissolved in 1800 g of water and admixed with 198.5 g (2.54 mol) of aluminum hydroxide by stirring. The mixture is then heated to 90° C. and stirred for 50 hours. It is then filtered with suction and the filter residue is dried in a vacuum drying cabinet to leave 962 g of a pale yellowish white powder which has no melting point below 360° C. The yield is about 100% of theory.

1.3. Preparation of the aluminum salt of 1-hydroxy-1H-phospholane 1-oxide 60 g of 1-hydroxy-1H-phospholane 1-oxide are dissolved in 95 ml of water and heated to 85° C. with stirring. 13 g (0.167 mol) of aluminum hydroxide are then added, and the mixture is maintained at 85° C. for about 20 hours. It is then filtered with suction and the filter residue dried to leave 58 g of a white powder which has no melting point below 360° C. The yield is about 91% of theory.

1.4. Preparation of the aluminum salt of 1-hydroxy-3-methyl-2,5-dihydro-1H-phosphole 1-oxide 25 g (0.189 mol) of 1-hydroxy-3-methyl-2,5-dihydro-1H-phosphole 1-oxide are introduced into 50 ml of water and stirred under reflux with 4.9 g (0.063 mol) of aluminum hydroxide for 30 hours. This is followed by filtration with suction, and the filter residue is dried for four days at 140° C. in a vacuum drying cabinet to leave 25 g of a white powder which has no melting point below 360° C. The yield is 94% of theory.

2. Production and Testing of Flame-Retardant Polyester

The phosphorus compounds (salts) were mixed with the polymer and incorporated on a commercially available twin-screw compounder. In the case of glass fiber reinforced formulations, customary glass fibers for polyester were metered into the melt.

The melt temperatures during the compounding were about 250° C. in the case of polybutylene terephthalate (PBT). The test specimens were produced on an injection molding machine to ISO 7792-2.

Test specimens of each mixture were used to determine the UL 94 (Underwriters Laboratories) fire resistance classification on test specimens 1.2 mm in thickness and the breaking strength and breaking extension by the method of ISO 527.

2.1 PBT and the aluminum salt of 1-hydroxy-2,5-dihydro-1H-phosphole 1-oxide (prepared according to Example 1.1) were used to produce compounds with 30% by weight of glass fiber reinforcement without any further additives, the compounds were used to form injection molding test specimens, and these test specimens were tested with the following results:

| Concentration of Al salt % | UL 94 materials classification | Breaking strength N/mm² | Breaking extension % |
| --- | --- | --- | --- |
| 20 | V-0 | 116 | 1.9 |
| 17.5 | V-1 | 119 | 1.9 |
| 15 | V-2 | 131 | 2.1 |
| 12.5 | V-2 | 134 | 2.5 |

2.2 PBT and the aluminum salt of 1-hydroxy-3-methyl-2,5-dihydro-1H-phosphole 1-oxide (prepared according to Example 1.4) were used to produce compounds with 30% by weight of glass fiber reinforcement without any further additions, the compounds were used to form injection-molded test specimens, and these test specimens were tested with the following results:

| UL 94 | V-0 (0.8 mm) |
| --- | --- |
| Concentration | Materials classification |
| Aluminum salt | UL 94 |
| 20% | V-0 |

We claim:

1. A method for improving the flame retardancy of a polymer, the method comprising incorporating into the polymer an aluminum salt comprising a reaction product of a phosphorous compound with an aluminum compound, the phosphorous compound comprising at least one of 1-hydroxydihydrophosphole oxide and 1-hydroxyphospholane oxide, the aluminum compound comprising aluminum carbonate, aluminum hydroxide or aluminum oxide, wherein the phosphorous compound to the aluminum compound are reacted in at least a 3:1 molar ratio, each aluminum valence being occupied by the phosphorous compound, and wherein the aluminum salt has at least one of the formulas (Ia'), (Ib') and (II'):

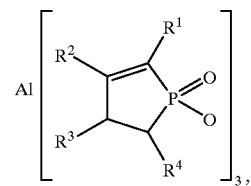

(Ia')

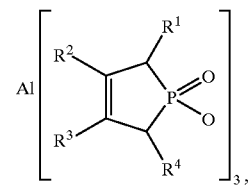

(Ib')

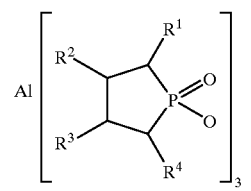

(II')

where $R^1$, $R^2$, $R^3$, and $R^4$ are, independently of each other, hydrogen or a straight-chain or branched alkyl group.

2. The method of claim 1, wherein the aluminum compound is aluminum hydroxide.

3. The method of claim 2, wherein the polymer is polyoxymnethylene, a polyester, or a polyamide.

4. The method of claim 3, wherein the polyester is polyethylene terephthalate or polybutylene terephthalate.

5. The method of claim 3, wherein the polyamide is nylon 46 or nylon 66.

6. The method of claim 2, wherein the phosphorous compound is:

1-hydroxy-3-alkyl-2,3-dihydro-1H-phosphole 1-oxide, 1-hydroxy-3-methyl-2,5-dihydro-1H-phosphole 1-oxide, 1-hydroxy-2,3-dihydro-1H-phosphole 1-oxide, 1-hydroxy-2,5-dihydro-1H-phosphole 1-oxide, 1-hydroxy-1H-phospholane 1-oxide, 1-hydroxy-3-methyl-1H-phospholane 1-oxide, or a mixture thereof.

7. The method of claim 2, wherein the straight-chain or branched alkyl group is a $C_1$–$C_{12}$-alkyl group.

8. The method of claim 7, wherein the $C_1$–$C_{12}$-alkyl group is a methyl or ethyl group.

9. A flame-retardant polymer prepared by incorporating therein an aluminum salt comprising a reaction product of a phosphorous compound with an aluminum compound, the phosphorous compound comprising at least one of 1-hydroxydihydrophosphole oxide and 1-hydroxyphospholane oxide, the aluminum compound comprising aluminum carbonate, aluminum hydroxide or aluminum oxide, wherein the phosphorous compound to the aluminum compound are reacted in at least a 3:1 molar ratio, each aluminum valence being occupied by the phosphorous compound, and wherein the aluminum salt has at least one of the formulas (Ia'), (Ib') and (II'):

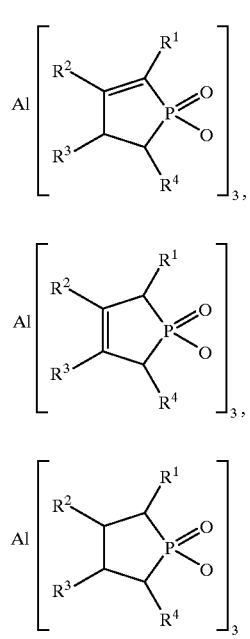

where $R^1$, $R^2$, $R^3$, and $R^4$ are, independently of each other, hydrogen or a straight-chain or branched alkyl group.

10. The flame-retardant polymer of claim 9, wherein the aluminum compound is aluminum hydroxide.

11. The flame-retardant polymer of claim 10, wherein the polymer is a condensation polymer.

12. The flame-retardant polymer of claim 10, wherein the polymer is polyethylene terephthalate or polybutylene terephthalate.

13. The flame-retardant polymer of claim 10, wherein the polymer is nylon 46 or nylon 66.

14. The flame-retardant polymer of claim 10, wherein the phosphorous compound is:

1-hydroxy-3-alkyl-2,3-dihydro-1H-phosphole 1-oxide, 1-hydroxy-3-methyl-2,5-dihydro-1H-phosphole 1-oxide, 1-hydroxy-2,3-dihydro-1H-phosphole 1-oxide, 1-hydroxy-2,5-dihydro-1H-phosphole 1-oxide, 1-hydroxy-1H-phospholane 1-oxide, 1-hydroxy-3-methyl-1H-phospholane 1-oxide, or a mixture thereof.

15. The flame-retardant polymer of claim 10, wherein the straight-chain alkyl group is a methyl or ethyl group.

16. A method for improving the flame retardancy of a polymer, the method comprising incorporating into the polymer an aluminum salt comprising a reaction product of a phosphorous compound with an aluminum compound, the phosphorous compound comprising at least one of 1-hydroxydihydrophosphole oxide and 1-hydroxyphospholane oxide, the aluminum compound comprising aluminum carbonate, aluminum hydroxide or aluminum oxide, wherein the phosphorous compound to the aluminum compound are reacted in about a 3:1 molar ratio, each aluminum valence being occupied by the phosphorous compound, and wherein the aluminum salt has at least one of the formulas (Ia'), (Ib') and (II'):

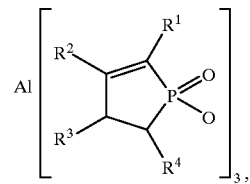

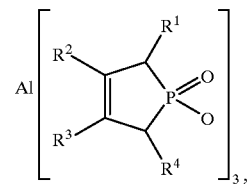

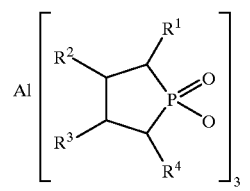

where $R^1$, $R^2$, $R^3$, and $R^4$ are, independently of each other, hydrogen or a straight-chain or branched alkyl group.

17. A flame-retardant polymer prepared by incorporating therein an aluminum salt comprising a reaction product of a phosphorous compound with an aluminum compound, the phosphorous compound comprising at least one of 1-hydroxydihydrophosphole oxide and 1-hydroxyphospholane oxide, the aluminum compound comprising aluminum carbonate, aluminum hydroxide or aluminum oxide, wherein the phosphorous compound to the aluminum compound are reacted in about a 3:1 molar ratio, each aluminum valence being occupied by the phosphorous compound, and wherein the aluminum salt has at least one of the formulas (Ia'), (Ib') and (II'):

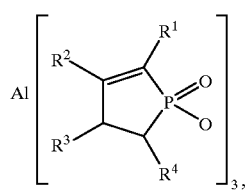
(Ia′)
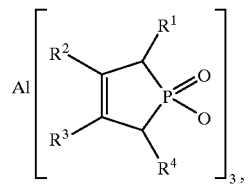
(Ib′)
-continued
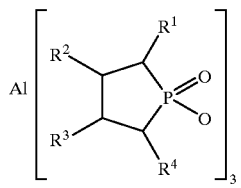
(II′)
where $R^1$, $R^2$, $R^3$, and $R^4$ are, independently of each other, hydrogen or a straight-chain or branched alkyl group.
\* \* \* \* \*